(12) United States Patent
Pai Raikar et al.

(10) Patent No.: US 12,327,351 B2
(45) Date of Patent: Jun. 10, 2025

(54) MEDICAL IMAGING SYSTEMS, DEVICES, AND METHODS FOR VISUALIZING A DEPLOYMENT STATE OF AN INTRACORPOREAL THERAPEUTIC DEVICE

(71) Applicant: KONINKLIJKE PHILIPS N.V., Eindhoven (NL)

(72) Inventors: Vipul Shrihari Pai Raikar, Somerville, MA (US); Maxim Fradkin, Maisons-Laffitte (FR); Benoit Jean-Dominique Bertrand Maurice Mory, Medford, MA (US); Kunal Vaidya, Boston, MA (US); Sibo Li, Waltham, MA (US); Grzegorz Andrzej Toporek, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 350 days.

(21) Appl. No.: 17/799,978

(22) PCT Filed: Feb. 12, 2021

(86) PCT No.: PCT/EP2021/053459
§ 371 (c)(1),
(2) Date: Aug. 16, 2022

(87) PCT Pub. No.: WO2021/165152
PCT Pub. Date: Aug. 26, 2021

(65) Prior Publication Data
US 2023/0074481 A1  Mar. 9, 2023

Related U.S. Application Data

(60) Provisional application No. 63/085,162, filed on Sep. 30, 2020.

(30) Foreign Application Priority Data

Feb. 18, 2020  (EP) .................................... 20290015

(51) Int. Cl.
  *G06T 7/00*  (2017.01)
  *A61F 2/24*  (2006.01)

(52) U.S. Cl.
  CPC ............ *G06T 7/0012* (2013.01); *A61F 2/246* (2013.01); *G06T 2207/10116* (2013.01); *G06T 2207/30048* (2013.01)

(58) Field of Classification Search
  CPC ......... G06T 7/0012; G06T 2207/10116; G06T 2207/30048; A61F 2/246
  See application file for complete search history.

(56) References Cited

U.S. PATENT DOCUMENTS

| 6,950,689 B1 | 9/2005 | Willis |
| 2008/0085042 A1* | 4/2008 | Trofimov ................ G06T 17/00 600/407 |

(Continued)

FOREIGN PATENT DOCUMENTS

| JP | 2019181213 A | 10/2019 |
| WO | 2018134140 A1 | 7/2018 |

(Continued)

OTHER PUBLICATIONS

International Search Report and Written Opinion for PCT/EP2021/053459; Mailing date: May 21, 2021, 11 pages.

(Continued)

*Primary Examiner* — John J Lee

(57) ABSTRACT

An end effector state estimation system for use in minimally invasive surgery (MIS) applications performs sensing and prediction algorithms to determine and visualize the state of an implantable therapeutic device during deployment. The end effector state estimation system includes a flexible (Continued)

elongate member, a therapeutic device coupled to a distal portion of the flexible elongate member, a sensor that measures at least one parameter related to the deployment state of the therapeutic device, and a processor. The processor receives image data from an imaging system representative of the therapeutic device positioned within the body cavity of the patient and the at least one parameter from the sensor, determines the deployment state of the therapeutic device based on the image data and the at least one parameter, outputs a graphical representation of the deployment state of the therapeutic device.

20 Claims, 12 Drawing Sheets

(56) References Cited

U.S. PATENT DOCUMENTS

| | | | |
|---|---|---|---|
| 2013/0083980 A1 | 4/2013 | Barbot et al. | |
| 2014/0058407 A1* | 2/2014 | Tsekos | A61B 34/30 606/130 |
| 2014/0254908 A1* | 9/2014 | Strommer | G06T 7/0012 382/128 |

FOREIGN PATENT DOCUMENTS

| | | |
|---|---|---|
| WO | 2018236936 A1 | 12/2018 |
| WO | 2019175141 A1 | 9/2019 |
| WO | 2020173814 A1 | 9/2020 |
| WO | 2020173815 A1 | 9/2020 |
| WO | 2020173816 A1 | 9/2020 |
| WO | 2021165165 A1 | 8/2021 |

OTHER PUBLICATIONS

Currie, M.E. et al., "Augmented Reality System for Ultrasound Guidance of Transcatheter Aortic Valve Implantation", Innovations (Phila), 2016, vol. 11, No. 1, pp. 31-39.

Eleid, M.F. et al., "The Learning Curve for Transcatheter Mitral Valve Repair With MitraClip", J Interv Cardiol, 2016, vol. 29, Issue 5, pp. 539-545.

Lee, M. C. H. et al., "TeTrIS: Template Transformer Networks for Image Segmentation With Shape Priors," IEEE Trans. Med. Imaging, 2019, vol. 38, No. 11, pp. 2596-2606.

* cited by examiner

MEDICAL IMAGING SYSTEMS, DEVICES, AND METHODS FOR VISUALIZING A DEPLOYMENT STATE OF AN INTRACORPOREAL THERAPEUTIC DEVICE

CROSS-REFERENCE TO PRIOR APPLICATIONS

This application is the U.S. National Phase application under 35 U.S.C. § 371 of International Application No. PCT/EP2021/053459, filed on Feb. 12, 2021, which claims the benefit of U.S. Provisional Patent Application No. 63/085,162, filed Sep. 30, 2020, and European Patent Application No. 20290015.5, filed on Feb. 18, 2020. These applications are hereby incorporated by reference herein.

TECHNICAL FIELD

The subject matter described herein relates to medical imaging systems, devices, and methods for estimating and visualizing a deployment state of intracorporal therapeutic devices. Using medical imaging to estimate and visualize a therapeutic device deployment state has particular but not exclusive utility for intracardiac transcatheter mitral valve repair procedures.

BACKGROUND

Mitral valve (MV) disease is among the most common valvular pathologies of the human heart, second only to aortic valve stenosis. The MV is a bi-leaflet valve on the left side of the heart, and is responsible for maintaining the unidirectional flow of blood from the left atrium (LA) to the left ventricle (LV). Functional wear on the valve tissue, or pathologies such as calcification, can lead to degradation of the valvular leaflets, resulting in improper coaptation of the leaflets. As a result, during LV compression, there is regurgitant blood flow from the LV back into the LA. This is known as mitral regurgitation (MR), and may result in a reduced output of the heart's pumping mechanism which, if left untreated, can lead to severe complications, including heart failure. The fundamental goal of treatment in MR patients is to reduce the MR to levels that restore heart function and improve the patient's overall quality of life.

With the advancement of minimally invasive therapies (e.g., minimally invasive surgery or MIS) replacing open surgeries, transcatheter mitral valve repair (TMVR) has emerged as a strong alternative therapy for patients at high risk from open surgery. Numerous devices exist for treating structural heart disease (SHD). One example TMVR device is a Mitral Valve Clip (MC) device. Clinical studies have shown MC to have a high efficacy in improving patient outcomes by reducing MR to acceptable levels. In addition, due to the transcatheter approach, the associated length of hospital stay is reduced as compared to open surgery. This, in turn, may drive a reduction in post-procedural complications, thereby improving patient outcomes as well as reducing the burden on hospital systems.

The use of procedures such as MC implantation is expected to increase over the next decade. However, currently, due to the complexity of the MC device and its delivery system, the procedures require highly skilled practitioners, both for operating the device and for interpreting the X-ray and ultrasound images that are important for navigation and deployment tasks. The procedure requires an experienced echocardiographer who can manipulate the ultrasound probe and imaging system to obtain high-quality images and views of the device with respect to the surrounding anatomy, to quickly identify the device and procedure state. The procedure also requires clear communication between team members, particularly for less experienced operators. This requires accurate representation of the device's end effector (e.g., the clip), which may be difficult to achieve for many combinations of device position, orientation, open/closed state, and other factors.

It should therefore be appreciated that such commonly used TMVR procedures have numerous drawbacks, including image capture, image interpretation, difficulty understanding the pose and state of the device's end effector, and otherwise. Accordingly, long-felt needs exist for improved TMVR systems and procedures that address the foregoing and other concerns.

The information included in this Background section of the specification, including any references cited herein and any description or discussion thereof, is included for technical reference purposes only and is not to be regarded as subject matter by which the scope of the disclosure is to be bound.

SUMMARY

Disclosed is an end effector state estimation system for use in transcatheter minimally invasive surgery (MIS) applications, which include sensing and prediction algorithms to determine the state of an implantable therapeutic device during the maneuvers associated with deployment, based on control inputs and/or imaging data, and annotation of medical images to include a graphical representation of the therapeutic device. It will be understood that, for the purposes of the present disclosure, a deployable therapeutic device, or a deployment assembly for deploying a therapeutic device, may be referred to as an end effector.

Structural heart procedures performed using transcatheter techniques are highly imaging-intensive procedures. Navigation, target selection, and deployment are more easily performed when real-time 3D imaging is available. However, the exact state of an end effector may be difficult to ascertain. The end effector state estimation system will enable procedures to be done in 3D with greater confidence, and reduce the cognitive burden on clinicians to find optimal 2D slices from 3D data.

A high-quality ultrasound image is dependent on optimal sonification of the objects of interest, but may suffer from image artifacts that interfere with the visualization of tissues and devices. The end effector state estimation system can help supplement the conventional imaging with accurate device state, thus improving confidence in the procedure and thus potentially improving outcomes and shortening learning curves. The end effector state estimation system disclosed herein has particular, but not exclusive, utility for intracardiac transcatheter mitral valve repair procedures.

According to an embodiment of the present disclosure, a system for determining a deployment state of a therapeutic device coupled to a distal portion of a flexible elongate member positioned within a body cavity of a patient is provided. The system includes at least one sensor configured to measure at least one parameter related to the deployment state of the therapeutic device; a processor configured to: receive: image data obtained by an imaging system, wherein the image data is representative of the therapeutic device positioned within the body cavity of the patient; and the at least one parameter; determine the deployment state of the therapeutic device based on the image data and the at least one parameter; and output, to a display in communication with the processor, a graphical representation of the deployment state of the therapeutic device.

In some embodiments, the processor is configured to output, to the display, a screen display comprising: an image of the body cavity of the patient generated based on the image data; and the graphical representation of the deployment state of the therapeutic device overlaid on the image of the body cavity. In some embodiments, the graphical representation of the deployment state of the therapeutic device comprises a visualization of a three-dimensional model of the therapeutic device. In some embodiments, the at least one parameter comprises at least one of a position or an angle of a control of the therapeutic device. In some embodiments, the system comprises a transcatheter delivery device, the transcatheter delivery device comprising the flexible elongate member, and wherein the at least one parameter comprises at least one of a position or an angle of the transcatheter delivery device. In some embodiments, the at least one sensor comprises an encoder coupled to a mechanical control of the transcatheter delivery device. In some embodiments, the at least one sensor comprises a magnetic sensor configured to measure the at least one parameter by obtaining position measurements of magnetic seeds positioned on the therapeutic device.

In some embodiments, the imaging system comprises an ultrasound imaging system. In some embodiments, the imaging system comprises an X-ray imaging system. In some embodiments, the processor is configured to determine the deployment state of the therapeutic device by using image recognition to match an image generated based on the image data to a model of the therapeutic device. In some embodiments, the at least one parameter comprises a deployment measurement, and wherein the processor is configured to: determine a confidence level of the matched model; and determine, when the confidence level is below a threshold value, the deployment state based on the deployment measurement.

According to another embodiment of the present disclosure, a method for determining a deployment state of a therapeutic device includes: with a sensor, measuring at least one parameter related to the deployment state of the therapeutic device, wherein sensor is coupled to a distal portion of a flexible elongate member; obtaining, with an imaging system, images including the therapeutic device; with a processor: determining the deployment state of the therapeutic device based on the images and the at least one parameter; and outputting, to a display in communication with the processor, a graphical representation of the deployment state of the therapeutic device.

In some embodiments, the method comprises outputting, to the display, a screen display comprising: at least one of the images; and the graphical representation of the deployment state of the therapeutic device overlaid on the at least one image. In some embodiments, the at least one parameter comprises a position or angle of a control of the flexible elongate member. In some embodiments, the at least one parameter comprises a position or angle of the therapeutic device. In some embodiments, the imaging system comprises an ultrasound imaging system. In some embodiments, the imaging system comprises an X-ray imaging system. In some embodiments, the sensor comprises a magnetic sensor, and wherein measuring the at least one parameter comprises obtaining position measurements of magnetic seeds positioned on the therapeutic device. In some embodiments, combining information from the sensor and the imaging system to determine the deployment state of the therapeutic device comprises using image recognition to match an image from the imaging system to a model of the therapeutic device.

According to another embodiment of the present disclosure, a system for determining a deployment state of a therapeutic device includes: a mitral valve clip placement device comprising: a catheter; and a mitral valve clip coupled to a distal portion of the catheter; an ultrasound imaging device configured to obtain ultrasound images of the mitral valve clip positioned within a body cavity of a patient; an X-ray imaging device configured to obtain X-ray images of the mitral valve clip positioned within the body cavity of the patient; a sensor coupled to the mitral valve clip placement device and configured to provide a sensor signal indicating a parameter related to the deployment state of the mitral valve clip; and a processor configured to: determine, based on the parameter and the X-ray images, a deployment state of the mitral valve clip; and output, to a display in communication with the processor: at least one of the ultrasound images; and a graphical representation of the deployment state of the therapeutic device.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the end effector state estimation system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
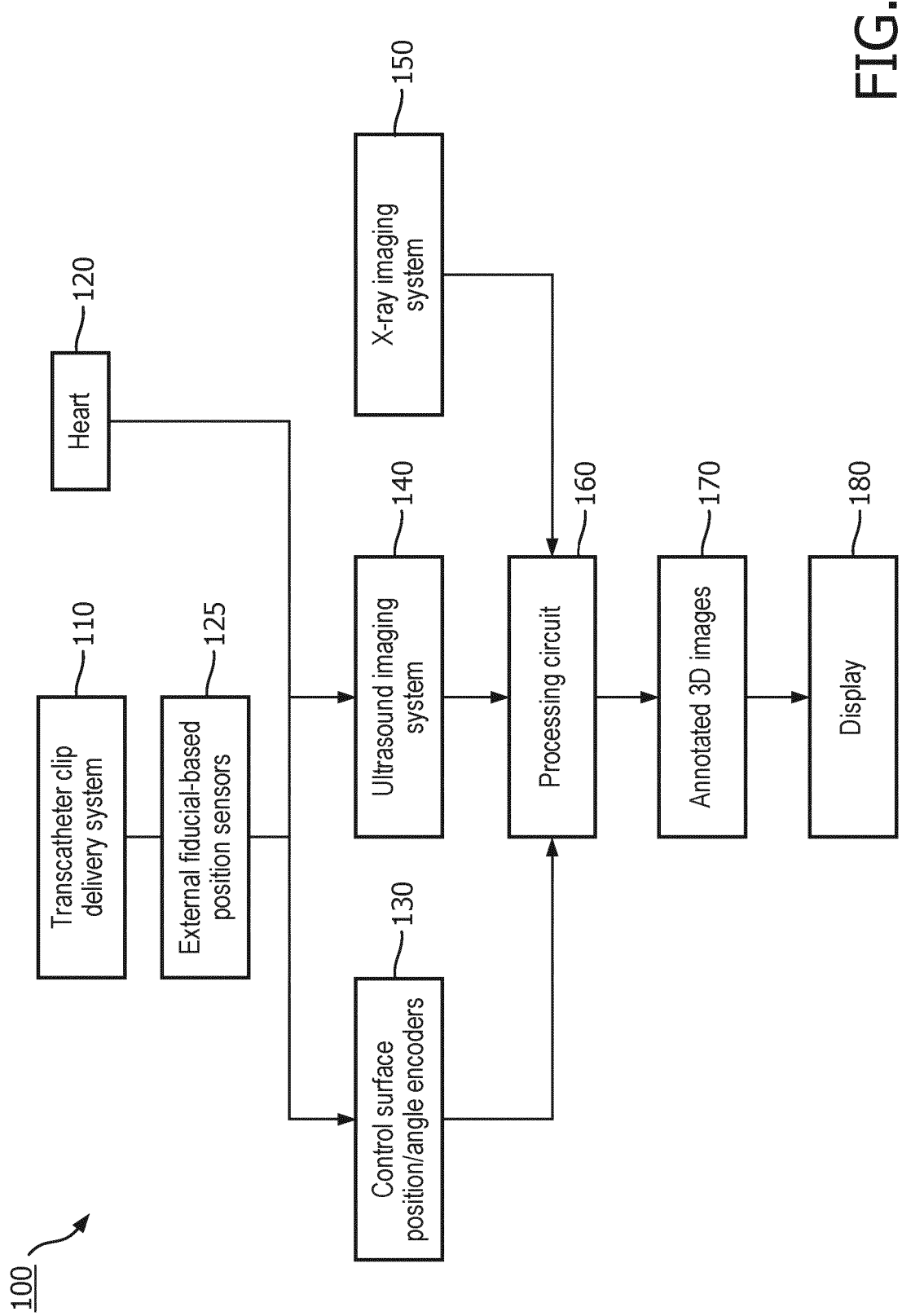
FIG. 1 is diagrammatic representation of an example end effector state estimation system in accordance with at least one embodiment of the present disclosure.

Disclosed is an end effector state estimation system for use in transcatheter minimally invasive surgery (MIS) applications. Disclosed are systems and methods to utilize sensing in the device manipulators (e.g., manual controls) in combination with machine-learning-based prediction to accurately acquire the state of an implantable therapeutic device during the maneuvers associated with deployment. Also disclosed are systems and methods to derive device state using image-based information, and combinations thereof. In various embodiments, a therapeutic device can be or can include an end effector. Aspects of the present disclosure may be applied to end effectors and/or therapeutic devices that are/include an end effector, including any suitable end effector and/or therapeutic device that expands, contracts, bends, flexes, articulates, or otherwise changes shape at a distal end, a proximal end, or at any point or points in between the proximal and distal ends.

Structural heart procedures performed using transcatheter techniques are highly imaging-intensive procedures. In particular, the mitral valve leaflet repair technique is driven by the need for high-quality dynamic (e.g., real time) imaging. X-ray images may clearly visualize the device but not the tissue of interest, whereas ultrasound images may show tissue but have a hard time clearly visualizing the device. 2D ultrasound and X-ray imaging guidance may be used during the procedure, but this essentially involves trying to solve a 3D problem in two dimensions. There is mounting evidence that navigation, target selection, and deployment are more easily performed when real-time 3D imaging is available. However, even with 3D imaging, the exact orientation and open/close state of an end effector may be difficult to ascertain, relative to the tissues of concern. The end effector state estimation system of the present disclosure will enable procedures to be done in 3D with greater confidence, and may also permit the use of 2D images that are improved through the analysis of 3D information. The end effector state estimation system may also reduce the cognitive burden on the ultrasound operator to find optimal 2D slices for portraying the 3D state of the transcatheter device's end effector.

A high-quality ultrasound image is dependent on optimal sonification of the objects of interest (e.g., the mitral valve leaflets and the clip or other end effector for the transcatheter device). Ultrasound imaging can suffer from artifacts such as acoustic dropout, shadowing, bloom artifacts due to improper gain, etc., which can complicate the clear, visualization of tissues and devices in the same image. The end effector state estimation system can help supplement the conventional imaging with accurate device state, even when such artifacts disturb the image.

An important task in leaflet repair using clip-type devices is the proper grasping of the individual leaflets within the gripping mechanism of the clip. Oftentimes, gain is increased to aid in ultrasound imaging of the mitral valve leaflets, which can then interfere with visualization of the slender gripping arms of the clip. However, proper understanding of the clip's open/closed state is important to performing the procedure. The end effector state estimation system can provide this information, thus improving confidence in the procedure and potentially improving outcomes and reducing procedure times.

As described above, MIS procedures such as transcatheter intracardiac treatments are driven by the quality of imaging, and by effective communication between the team of clinicians performing the procedure. This comes with an associated learning curve, such that many procedures may need to be performed by team members before high proficiency is achieved. The end effector state estimation system is able to provide feedback to the team, including device state and pose, thereby potentially improving the learning curve and increasing confidence during the procedure.

The present disclosure aids substantially in the performance of minimally invasive surgery (MIS), by improving the visualization of a device end effector. Implemented on a processor in communication with a transcatheter device control system and one or more external imaging systems, the end effector state estimation system disclosed herein provides practical enhancement or annotation of live ultrasound images during a MIS procedure. This augmented visualization allows for other imaging modalities offering varying degrees of clarity and precision to be used, and enables lower-skilled operators to perform transcatheter therapeutic procedures. This unconventional approach improves the functioning of the transcatheter device control system, by making the system easier to operate for complex tasks such as intracardiac repair procedures.

The end effector state estimation system may generate real-time image enhancements or annotations viewable on a display, and may be operated by a control process executing on a processor that accepts user inputs from a keyboard, mouse, or touchscreen interface, and that may be in communication with one or more medical instruments. In that regard, the control process performs certain specific operations in response to different inputs or selections made at different times and in response to different stimuli. Certain structures, functions, and operations of the processor, display, sensors, and user input systems are known in the art, while others are recited herein to enable novel features or aspects of the present disclosure with particularity.

These descriptions are provided for exemplary purposes only, and should not be considered to limit the scope of the end effector state estimation system. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is diagrammatic representation of an example therapeutic device state estimation system 100, which may also be referred to as an end effector state estimation system, in accordance with at least one embodiment of the present disclosure. The example end effector state estimation system 100 may be configured to assist clinicians in the operation of a transcatheter clip delivery system 110 (e.g., the MitraClip or TriClip from Abbott, or the Pascal system from Edwards Life Sciences) which is configured to maneuver a clip or other related end effector device within a heart 120. The end effector state estimation system 100 receives data from external fiducial-based position sensors 125 (e.g., magnetic position sensors, optical position sensors), position or angle encoders 130 or related sensors, an ultrasound imaging system 140, and/or an X-ray imaging system 150.

The end effector state estimation system 100 also includes a processing circuit 160. In the example shown in FIG. 1, the processing circuit 160 is capable of interfacing with and/or acting as a control unit for reading encoder information from the sensors 130 positioned on the mechanical manipulator, or from spatial localization systems. The sensor(s) 130 can measure one or a plurality of parameters related to the deployment state of a therapeutic clip device delivered using the transcatheter clip delivery system 110. The processing circuit 160 is further capable of running conventional data (image, signal) processing algorithms and/or machine learning and deep learning algorithms on image data from the ultrasound imaging system 140 and/or X-ray imaging system 150. The processing circuit 160 is additionally capable of generating complex, annotated 2D or 3D renderings 170 and showing them on a display 180, e.g., with multi-channel rendering support. In some embodiments, the processing circuit comprises a single processing component disposed within a housing. In other embodiments, the processing component comprises multiple hardware components and/or hardware components, such as a central processing unit (CPU), graphics processing unit (GPU), or any other suitable component positioned within a single housing, or distributed among multiple housings.

It will be understood that the examples described above are provided for purposes of illustration, and are not intended to be limiting. Other devices and/or device configurations may be utilized to carry out the operations described herein.

Figure 2:
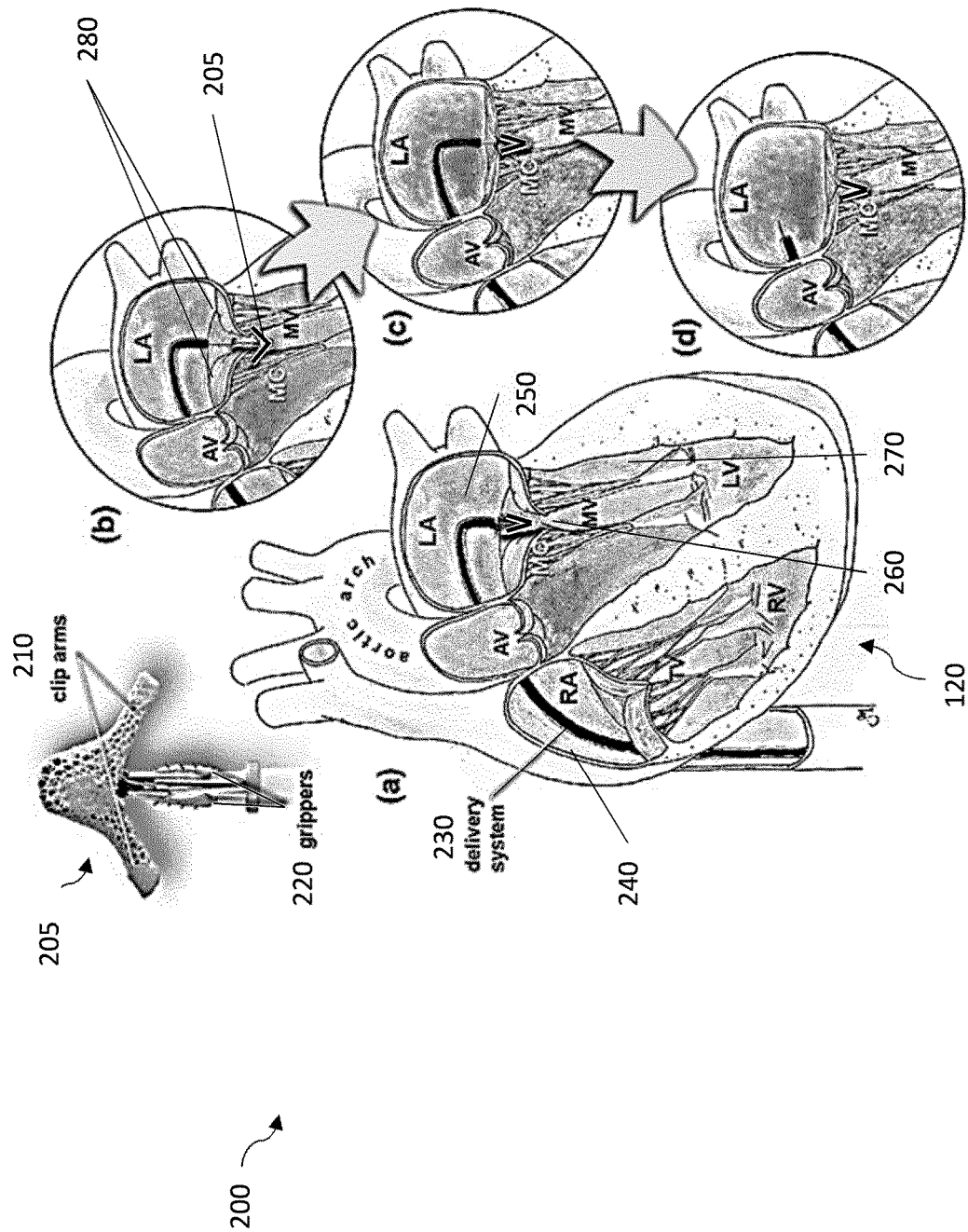
FIG. 2 is a diagrammatic representation of an example transcatheter mitral valve repair procedure in accordance with at least one embodiment of the present disclosure.

FIG. 2 is a diagrammatic representation of an example transcatheter mitral valve repair (TMVR) procedure 200 in accordance with at least one embodiment of the present disclosure. The procedure 200 employs a clip device 205 (e.g., the Abbott MitraClip) that includes two arms 210 and two grippers 220. The procedure also includes using a catheter-based delivery system 230 that uses a flexible elongate member to enter the heart 120 through the right atrium 240, then punctures the right atrium 240 to enter the left atrium 250, and proceeds through the mitral valve 260 into the left ventricle 270 (step "a"). The clip 205 is then opened (step "b"), and subsequently closed such that it grips the two leaflets 280 of the mitral valve 260 (step "c"). The clip 205 is then detached from the delivery system 230 (step "d"), and the delivery system 230 is withdrawn from the heart 120. The clip device 205 can be referenced as a therapeutic device and/or an end effector of the delivery system 230. A person of ordinary skill in the art will appreciate that other devices and procedures may be employed to repair structures within the heart 120, e.g. for valve replacement, tissue ablation, installation or removal of pacemaker components, etc., and may be employed along with the end effector state estimation system, so long as the device includes an end effector large and acoustically reflective enough to be visualized by ultrasound images.

Positioning and deploying a therapeutic device, such as a mitral valve clip, in the mitral valve is a challenging procedure. In this regard, the mitral valve is typically still operating while the procedure is performed. Although X-ray imaging data may provide a clear image of the mitral valve clip and delivery system, the device's position with respect to the mitral valve may not be visible in the X-ray image. Although ultrasound may provide more anatomical information and details such as the mitral valve, the echogenicity of the mitral valve clip and delivery system may be such that it is difficult to provide images with the proper gain, contrast, and other image settings to clearly visualize the location and deployment state of the mitral valve clip with sufficient precision to carry out the procedure. Further, if two-dimensional ultrasound imaging is used, it may be difficult to determine the orientation of the mitral clip with respect to the field of view of the ultrasound probe regardless of the image settings.

Figure 3:
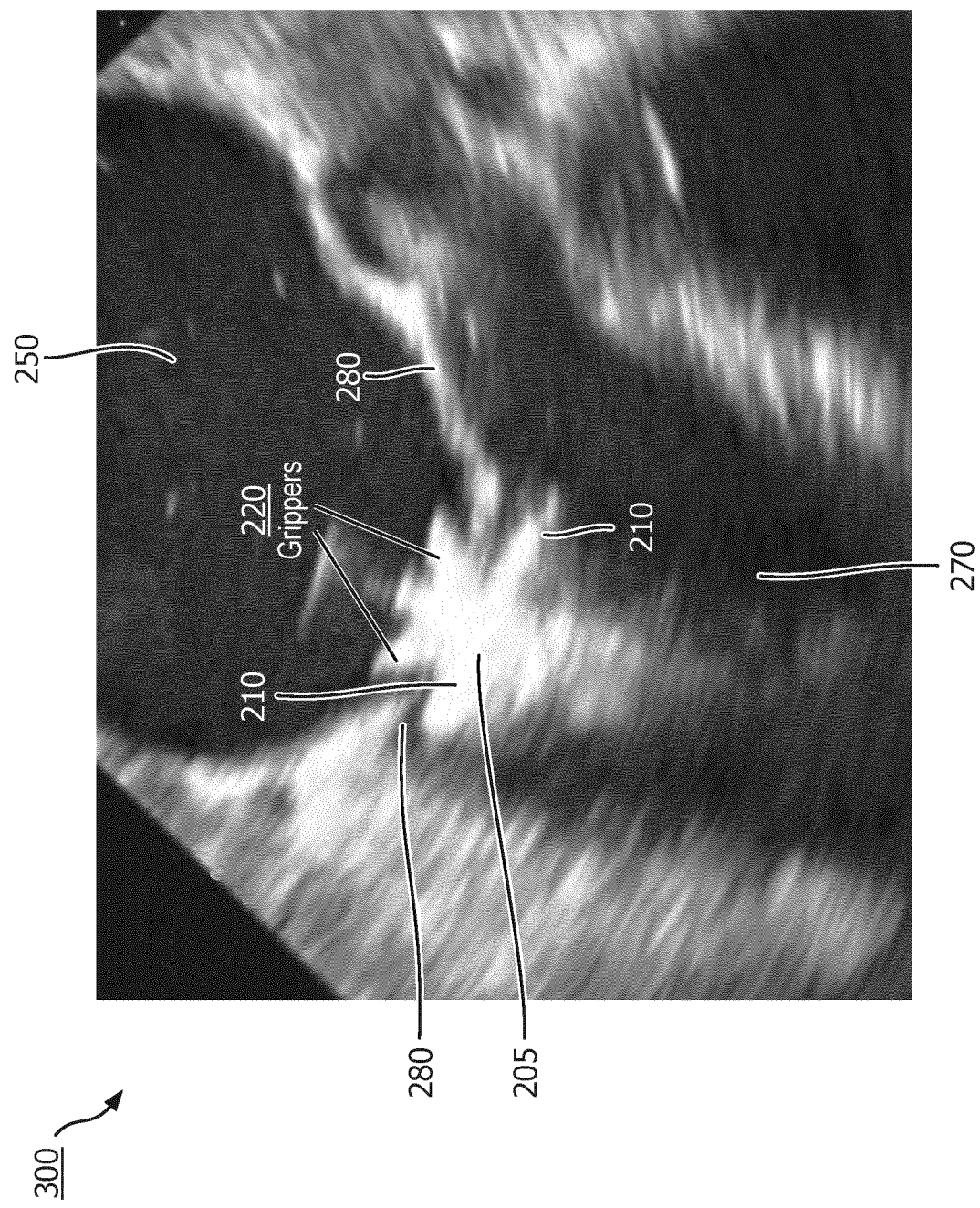
FIG. 3 is an ultrasound image of an example transcatheter mitral valve repair procedure in accordance with at least one embodiment of the present disclosure.

In this regard, FIG. 3 is an ultrasound image 300 of an example transcatheter mitral valve repair (TMVR) procedure in accordance with at least one embodiment of the present disclosure. Such images may be captured for example using a trans-esophageal echocardiogram (TEE) probe. Thresholding and/or edge gradient filtering may be employed to reject noise in the image and to enhance the contrast between tissue, blood, and solid components of the treatment device.

Visible in the image 300 are the mitral valve clip 205, the left atrium 250, the left ventricle 270, the mitral valve leaflets 280, and the arms 210 and grippers 220 of the mitral valve clip 205. During the TMVR procedure, it may be desirable for example to position the clip 205 such that the arms 210 are located in the left ventricle 270, the grippers 220 are located in the left atrium 250, and the leaflets 280 each fall between an arm 210 and a gripper 220. In this configuration, the clip 205 can be closed such that it permanently holds the leaflets 280 together. This can limit mitral regurgitation (MR), thus improving the health of an MR patient.

For many clinicians it may be quite challenging to capture real-time ultrasound images that include both leaflets 280, both arms 210, and both grippers 220, as seen in the example image 300 of FIG. 3. To capture such an image of a beating heart involves proper position and orientation of an ultrasound probe, proper gain settings to show the leaflets 280, and yet an absence of noise, shadow, and bloom artifacts to show the structure of the clip 205. The imaging clinician must also select, in real time, a 2D slice of the 3D volume data where these features are located. It is a feature of the present disclosure to reduce the burden on imaging clinicians by permitting the position, orientation, and open/closed state of the clip (or other end effector) to be determined and visually reported without the need for real-time, manually optimized ultrasound images.

Figure 4:
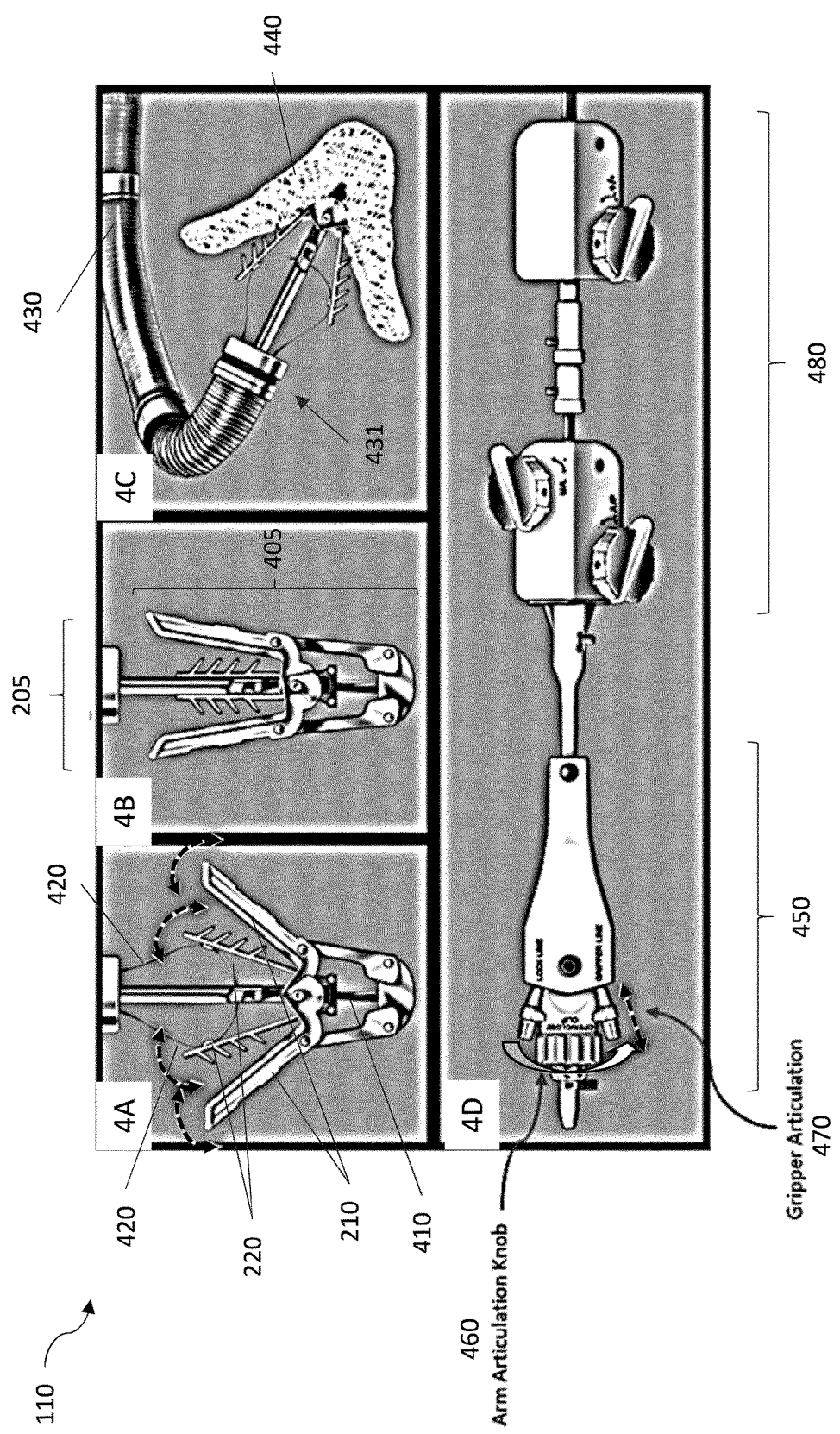
FIG. 4 is a diagrammatic view of an example transcatheter clip delivery system in accordance with at least one embodiment of the present disclosure.

FIG. 4 is a diagrammatic view of an example transcatheter clip delivery system 110 in accordance with at least one embodiment of the present disclosure. Visible are the clip 205, including the arms 210 and grippers 220. The arms 210 are operated by an actuator 410, while the grippers 220 are operated by tendons 420. Both the tendons 420 and the actuator 410 are threaded through a catheter or flexible elongate member 430. The clip 205 can be coupled to a distal portion 431 of the flexible elongate member 430 and may considered an end effector. FIG. 4A shows the clip 205 in a partially open configuration. FIG. 4B shows the clip 205 in a closed configuration. In some aspects, the clip 205 may be advanced through the mitral valve in the closed configuration, and then opened as shown in FIG. 4A to engage the leaflets of the mitral valve. Then, the grippers 220 can be opened and brought closer to the arms 210 to clamp onto opposing leaflets of the mitral valve between the arms 210 and grippers 220. FIG. 4C shows the clip 205 covered by a fabric cover 440, which may encourage the growth of tissue over the clip 205 once it is implanted in the mitral valve of a patient. FIG. 4D shows clip controls 450 and delivery system controls 480 of the example delivery system 110. The clip controls 450 include an arm articulation knob 460 and a pair of individual gripper articulators 470. The open-close state of the arms 210 and grippers 220 may be referred to as parameters related to a deployment state of the clip device 205.

Figure 5:
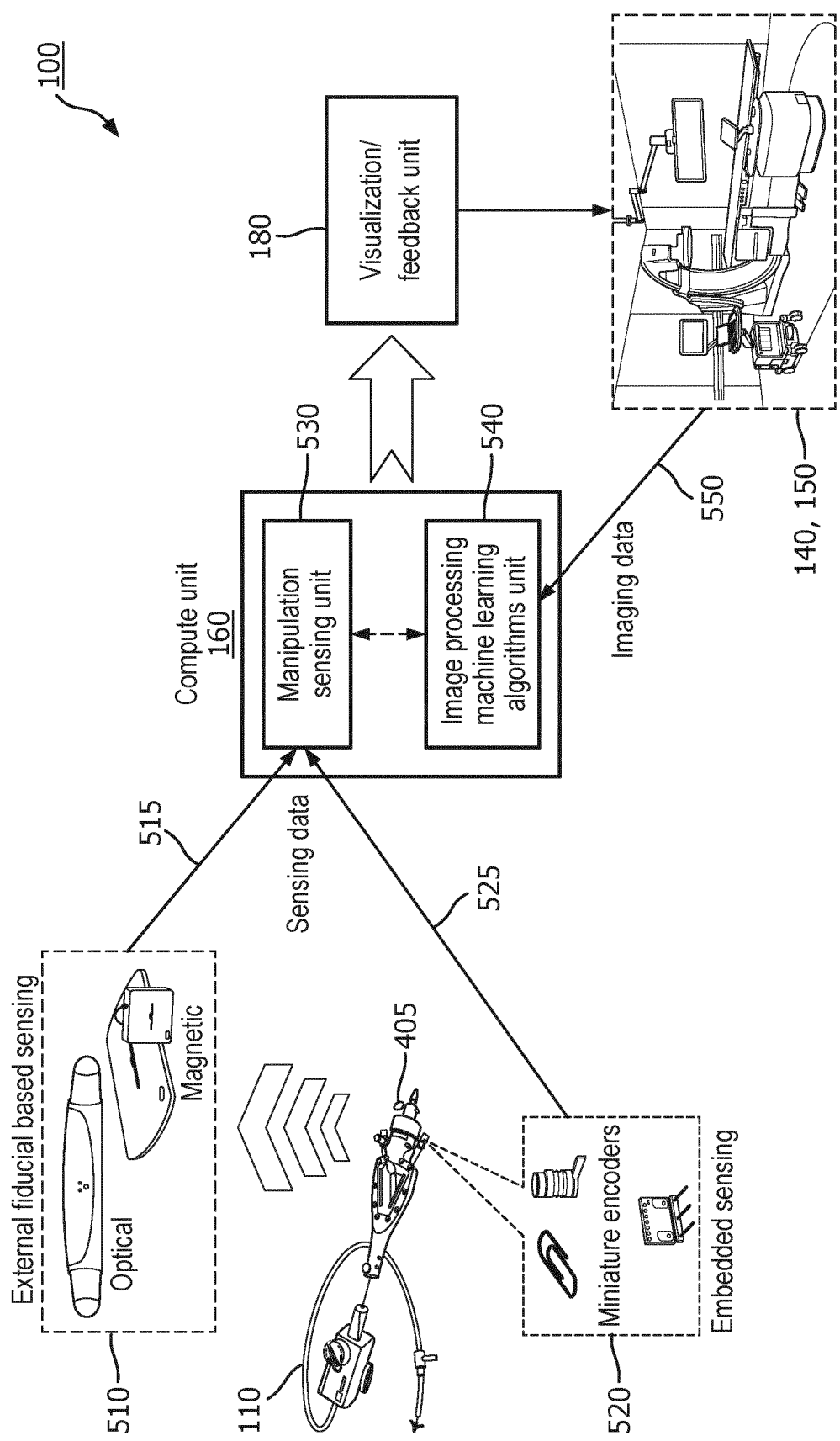
FIG. 5 is a diagrammatic view of an example end effector state estimation system 100, in accordance with at least one embodiment of the present disclosure.

FIG. 5 is a diagrammatic view of an example end effector state estimation system 100, in accordance with at least one embodiment of the present disclosure. The mechanical manipulators 450 on the clip delivery system 110 are used to control the articulation of the valve repair device (e.g., a clip 205 which is part of the detachable end-effector 405, as shown for example in FIG. 4). To sense or encode the articulation based on the mechanical manipulation on the handle of the clip delivery system, sensors 510 and/or 520 can be employed to detect the state of controls such as the arm articulation knob 460 and the gripper articulators 470. The sensors 510 or 520 may produce digitized, machine-readable signals, and may include, but are not limited to, electrical encoders (e.g., rotary encoder), optical encoders, potentiometers for embedded sensing, magnetic spatial localization systems (e.g., to track control surfaces, actuators, or tendons with one or more magnetic seeds), IR-based active or passive optical spatial localization systems (e.g., to track the position of one or more IR-reflecting or IR-emitting fiducial markers), a vision-based (e.g., RGB, monochrome, etc.) based optical tracking system to localize the positions of one or more visible fiducial features.

The digitized signals (e.g., signals 515 or 525) are received in a manipulation sensing unit 530 of a computation unit corresponding to the processing circuit 160 (FIG. 1). The computation unit 160 also includes an image processing (e.g., machine learning algorithms) unit 540 that receives imaging data 550 from an imaging system 140 or 150. The computation unit 160 has an interface (e.g., software and/or hardware) to process relevant information to feed into one or more algorithms. For example, the variable α may be assigned for the knob position controlling the arms of the "clip" device and β for the manipulator position controlling the grippers. The algorithm or algorithms are designed to produce information that most closely closest represents the physical articulation of the device inside the body using two sources of input: (1) signals describing the current state of manipulation on the device handle (α, β), and (2). imaging information from intraprocedural ultrasound, X-ray, or a fusion of the two real-time interventional imaging modalities:

$I_{us}$, $I_{x-ray}$, $I_{us+x-ray}$.

The algorithms can consist of, but are not limited to, the following types of fundamental modules. In some embodiments, the signals are received, digitized, and/or processed by an interface device or control unit in communication with the processor 160, and the interface device provides positional information based on the received signals to the processor 160.

For therapeutic devices such as a mitral valve clip, the physical device state, which varies from fully closed to fully open, may be controlled by a screw and tendon driven system. While control of such devices may be for only one degree-of-freedom (DOF) (e.g., manipulator state α maps to the state of clip opening and similarly, β for gripper state), the response of opening and closing might not predictably or repeatably map to the one DOF articulation. A lookup table relating specific control surface settings to particular device states may therefore not be a reliable predictor of device state in all cases. This challenge with mathematically modeling the relationship is caused by the physical properties of the device delivery system and the influence that its operating environment has on these physical properties. For example, the hysteresis of this system can be modeled in a data-driven manner. U.S. Provisional Application No. 62/825,914, filed Mar. 29, 2019, U.S. Provisional Application No. 62/825,905, filed Mar. 29, 2019, and U.S. Provisional Application No. 62/811,705, filed Feb. 28, 2019, which are hereby incorporated by reference in their entireties, describe methods for estimating the kinematics of electro mechanical devices. These techniques can be applied to deriving the state of the implantable end-effector prior to deployment.

One method to account for discrepancies between control state information (e.g., encoder feedback) and the actual position or deployment state of the therapeutic device is to utilize a neural network to regress a state θ (e.g., an angle in deg.) of the device arms with respect to the knob rotations α. The data collection for this can be done by placing magnetic tracking seeds (e.g., five DOF, —5 mm) on the arms and collecting data for (a.) the digital signal from knob manipulation quantized to a desired range sensitive enough for the application, and (b.) the arm location position, converted into an angle value. This can be then solved as a regression problem. Data acquisition can also be achieved in a controlled, robotic manner (e.g., moving knobs or other control surfaces back and forth in different combinations and recording the effects on device state). The above techniques also apply to the other articulations (e.g., gripper articulation) as illustrated for example in FIG. 4.

Figure 6:
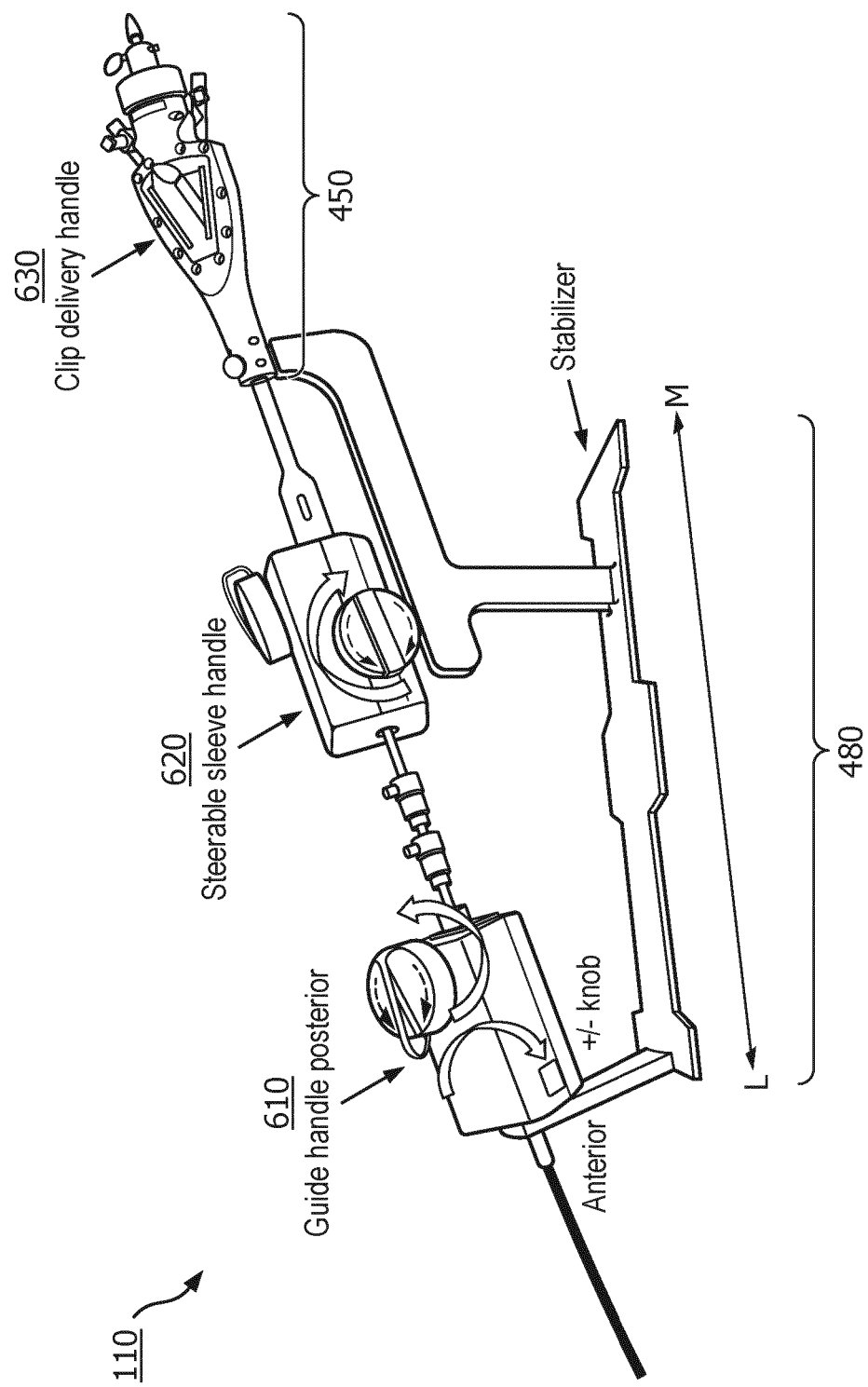
FIG. 6 is a perspective view of at least a portion of an example transcatheter clip delivery system 110 in accordance with at least one embodiment of the present disclosure.

FIG. 6 is a perspective view of at least a portion of an example transcatheter clip delivery system 110 in accordance with at least one embodiment of the present disclosure. The transcatheter clip delivery system 110 includes clip controls 450 and delivery system controls 480, housed in a guide handle 610, steerable sleeve handle 620, and clip delivery handle 630. As explained above, one or more sensors or encoders may be incorporated into any or all of the controls, such as the clip controls 450 and/or the delivery system controls 480, to provide positional and/or deployment state information about the end effector.

Figure 7:
FIG. 7 is an intraprocedural X-ray image from an example transcatheter mitral valve repair procedure, in accordance with at least one embodiment of the present disclosure.

FIG. 7 is an intraprocedural X-ray image 700 from an example transcatheter mitral valve repair (TMVR) procedure, in accordance with at least one embodiment of the present disclosure. X-ray images can be advantageous during MIS procedures, as from certain angles they may clearly show the position, orientation, and open/closed state of an end effector 405 (e.g., a clip 205) of a transcatheter delivery system 110. This may be represented for example as an angle θ that is measured or estimated, either manually by a clinician or automatically by an image recognition algorithm, based on the X-ray image 700. Angles may be determined for example through segmentation, force measurement, shape sensing, or by the user drawing the angle on a touchscreen. However, X-ray images may not show soft tissue such as mitral valve leaflets, which may limit the usefulness of intraprocedural X-ray imaging for steering and deployment of an end effector device 405 relative to the tissues of interest. Nevertheless, a device state (e.g., angle θ) obtained from intraprocedural X-ray images 700 may be used to replace, supplement, confirm or adjust a device state obtained through sensing of control surfaces in the delivery system 110. The device state (e.g., angle θ) may then be employed to aid in image recognition of the 3D position, 3D orientation, and open/close state of the end effector 405, as described below. In some embodiments, separate angular measurements may be obtained for different components such as the arms and gripper of a clip device 205.

Figure 8:
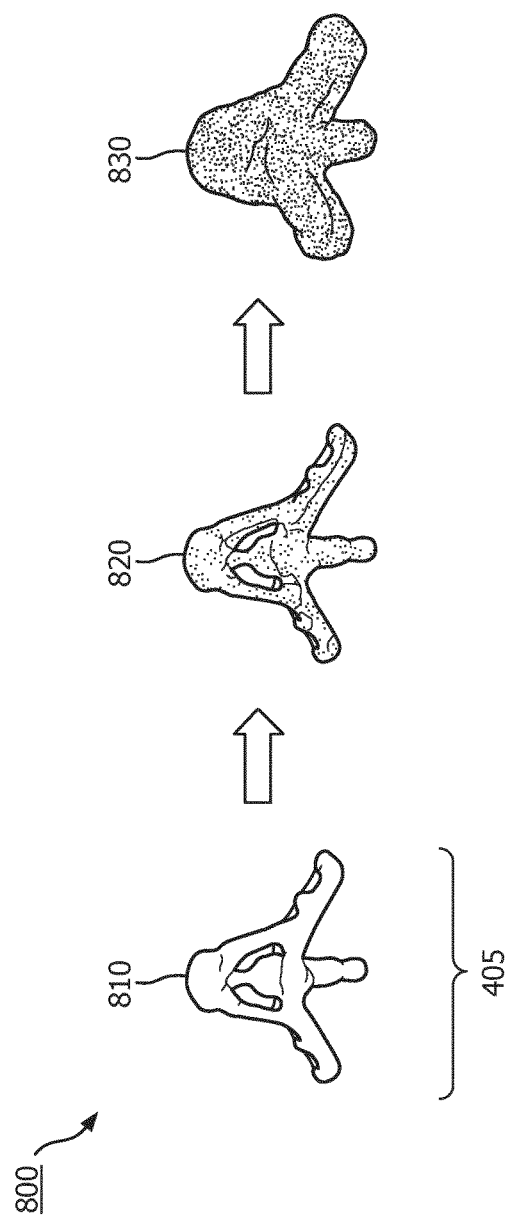
FIG. 8 is a perspective view of a 3D model of an end effector such as a mitral valve clip, in accordance with at least one embodiment of the present disclosure.

FIG. 8 is a perspective view of a 3D model 800 of an end effector 405 such as a mitral valve clip, in accordance with at least one embodiment of the present disclosure. The model includes a detailed version 810 that may for example resemble the appearance of the end effector in an X-ray image, a simplified version 830 that may for example resemble the appearance of the end effector in an ultrasound image, and an intermediate version 820 that may serve as a computational middle step for deriving a simplified model 830 from a detailed model 810.

Deployment of leaflet repair implants may be performed under live (e.g., real-time intraprocedural) X-ray and ultrasound guidance. These devices, when optimally visible, exhibit a clear profile and a predictable pattern in each imaging modality. These imaging features can be exploited to drive image-based algorithms (conventional deterministic image processing, machine learning, and/or combinations thereof) to capture the device state as well as predict device behavior. Since the physical and geometric relations of the device and its articulations are known a priori, this information can be incorporated into model-fitting algorithms. In this case, the algorithm utilizes conventional methods such as, but not limited to, level sets, active contours, active statistical shape and appearance models, etc. to fit a rigid model of the device in a discrete state. These device models can either be from a model family of discretized states or a continuous parametric model with a single degree of freedom (1 DOF) of articulation, or multiple degrees of freedom (e.g., 2 DOF, 3 DOF, etc.). A version of the algorithm is described below.

The end effector state estimation system 100 may be configured to fit a model of an interventional device (e.g., a mitral valve clip 205) to an ultrasound (US) image. This fit may involve aligning the 3D model 800 with the device depicted in the ultrasound image, referred to hereinafter as a "target". The model 800 may for example be represented as a triangular mesh, or by a binary mask, point cloud, etc., which can be transformed into triangular mesh by methods known in the art. Since the model 800 of the device end effector 405 is typically very detailed, while its representation in an ultrasound image is not, the model representation may be simplified using a method of mesh simplification known in the art. An example of model generation and simplification is shown in FIG. 8.

In examples where the model is rigid, it may be desirable to find a rigid transformation that allows for the best alignment of the model to the target, such as an Iterative Closest Point (ICP) algorithm. To define the correspondence between each mesh (M) point and the image (I), the target (T) points are defined by image thresholding. The threshold (th) can be either fixed or adaptive. Then, for each mesh point, the algorithm may for example determine the corresponding target along its surface normal (N):

$$T(p) = M(p) + \vec{N}(p) * d$$

where T(p) is a target point, M(p) is a mesh point and N(p) is a surface normal vector at point p. The algorithm may then define the signed magnitude of the displacement d as follows:

$$d = \begin{cases} (\max(I) - I(p))/\max(I), & \text{if } I(p) > th \\ \frac{I - \max(I)}{\max(I)}, & \text{elsewehere} \end{cases}$$

Once the correspondence between the mesh and target points has been determined, the algorithm may for example find a rigid transformation using single value decomposition (SVD). Then, the above step can be iteratively repeated until the process converges (i.e., the average distance between the mesh and the target points becomes negligible). In this manner, the end effector 405 (e.g., a mitral valve clip) can be located in an image (e.g., an X-ray or ultrasound image) in real time or near-real time, and its orientation determined. A person of ordinary skill in the art will appreciate that while this process is described for a single model, an algorithm can also determine the state of the end effector 405 by matching it against multiple models, each representing a different open/closed state, as described below.

Figure 9:
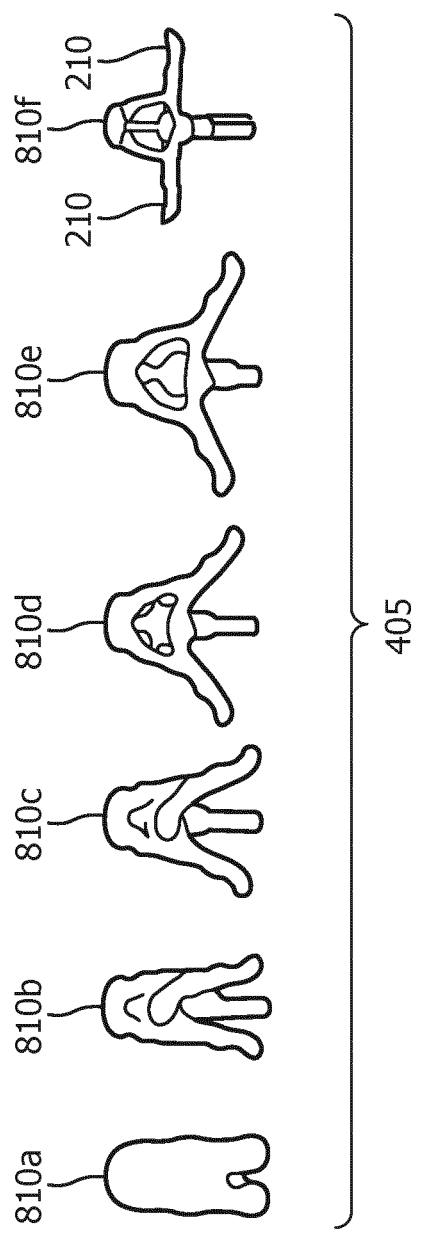
FIG. 9 is a perspective view showing detailed models of an end effector (e.g., a mitral valve clip) in six different open/closed states, in accordance with at least one embodiment of the present disclosure.

FIG. 9 is a perspective view showing models of an end effector 405 (e.g., a mitral valve clip) in six different open/closed states, in accordance with at least one embodiment of the present disclosure. In the case of a mitral valve clip and many other devices, their shape can change in the process of their deployment. For example, the mitral valve clip has arms 210 that can open and close to different orientations, as shown in FIG. 9. The models represented here include the arms 210, but not the grippers 220 (shown for example in FIGS. 2, 3, and 4). A person or ordinary skill in the art will appreciate that different models may include various permutations of arm and gripper positions, or other features of different end effectors 405. In the example shown in FIG. 9, model 8a represents an end effector 405 with fully closed arms 210, while model 810f represents an end effector 405 with fully open arms 210, and models 810b, 810c, 810d, and 810e represent different intermediate states between these two extremes.

Figure 10:
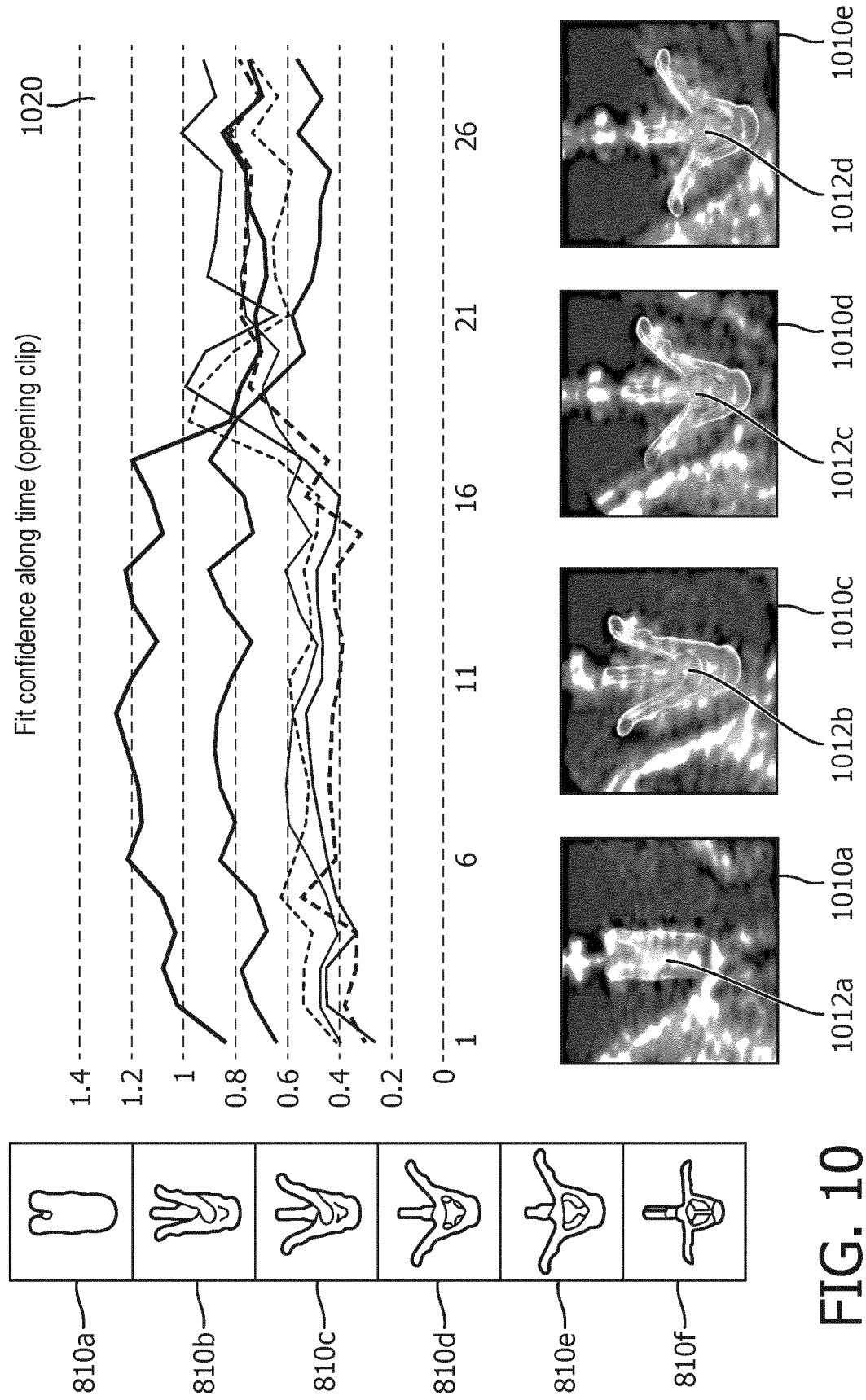
FIG. 10 is a diagrammatic representation of the inputs and outputs of an algorithm for matching ultrasound images to end effector models, in accordance with at least one embodiment of the present disclosure.

FIG. 10 is a diagrammatic representation of the inputs and outputs of an algorithm for matching ultrasound images to end effector models, in accordance with at least one embodiment of the present disclosure. These device models can either be from a model family of discretized states or a continuous parametric model with a single degree of freedom (1DOF) of articulation, or multiple degrees of freedom (e.g., 2 DOF, 3 DOF, etc.). In the example shown in FIG. 10, models 810a through 810f represent different open/closed states for the end effector. For a given ultrasound image (e.g., an instantaneous 3D snapshot of a volume of interest), each model is matched against the image data, and a confidence score is calculated, reflecting the probability that a given model accurately represents the device state shown in the image. An ordered group of models may be referred to as a Model Family (MF). Since it may be unknown which stage of device opening will be encountered in the first image frame, one possible approach consists of fitting all models of the MF using the algorithm explained hereinabove, and then choosing the one that fits best. In general, the model with the highest confidence score can be selected as the "true" or most probable current state of the end effector. This confidence score can be derived in several ways, primarily based on image features.

This choice can be made by defining a fitting confidence measure (CM). This CM can be defined as a weighted sum of two criteria: Dice coefficient and edge gradient measure. Dice coefficient (Dice), is based on the model and target volumes. The target volume is defined by thresholding the image in the region of interest (ROI) closely surrounding the fitted model. This measure is maximized when the mesh maximally overlaps the target. Edge gradient measure involves calculating a normalized sum of image gradients at all points of the fitted mesh. This measure is maximized when the mesh borders are best aligned with the image object borders. Alternatively or in addition, an appropriate model may be selected based on the control input positions and/or the X-ray images, as described above, or the user may select a model and a device position/orientation manually, either as a starting point or at intervals during the procedure.

Once a mechanism is defined to fit a MF to one frame, the image data can also be used for model tracking. Since the object movement is continuous between frames of the real-time ultrasound image sequence, model transformation from the previous frame can be used as an initial model pose in the next frame. The algorithm can also incorporate the knowledge that the model opening/closing is also continuous between the frames, therefore it isn't necessary to test the whole MF, but only the best model found in the previous frame and the "neighboring" models in the MF sequence. This approach may reduce the computational burden, making it more feasible for the algorithm to run in real time.

In the example shown in FIG. 10, ultrasound image 1010*a* corresponds to model 810*a*, and so the outlines of model 810*a* are overlaid onto the ultrasound image as graphical indicator 1012*a*. Image 1010*c* corresponds to, and had been overlaid with, a graphical indicator 1012*c* representative of model 810*c*, while images 1010*d* and 1010*e* have been overlaid with their corresponding graphical indicators 1012*d*, 1012*e*, representative of the models 810*d* and 810*e*, respectively. Since ultrasound images can be grainy, noisy, low-resolution, and prone to imaging artifacts, these overlaid models permit a clinician or other user to interpret, at a glance, the position, orientation, and open/closed state of the end effector in the ultrasound image, across a wide range of image quality. In some embodiments, the ultrasound images 1010 and their corresponding graphical indicators 1012 may be output as a graphical user interface or screen display and updated in real time to show the deployment state of the therapeutic device. In some embodiments, other types of graphical indicators or illustrations can be included in the screen display to indicate the deployment state, such as a wire frame illustration, a two-dimensional illustration, numerical indicators, textual indicators, and/or any other suitable type of graphical indicator. In some embodiments, an amount or percentage of deployment (e.g., angle, percent of maximum articulation) is displayed on the screen display. In some embodiments, the screen display includes a representation of the confidence of a position measurement, such as a numerical indicator, or a graphical representation similar or identical to the graph 1020. In some embodiments, the graphical indicator of the therapeutic device and/or a different indicator on the screen display may indicate the orientation of the therapeutic device with respect to the field of view of the image being used.

Selection and overlay of the most appropriate model can be greatly assisted, and computational burden correspondingly reduced, if the open/close state of the end effector is known, to within a certain degree of confidence, due to measurement of control surfaces (see FIG. 5) or X-ray images (see FIG. 7).

Figure 11:
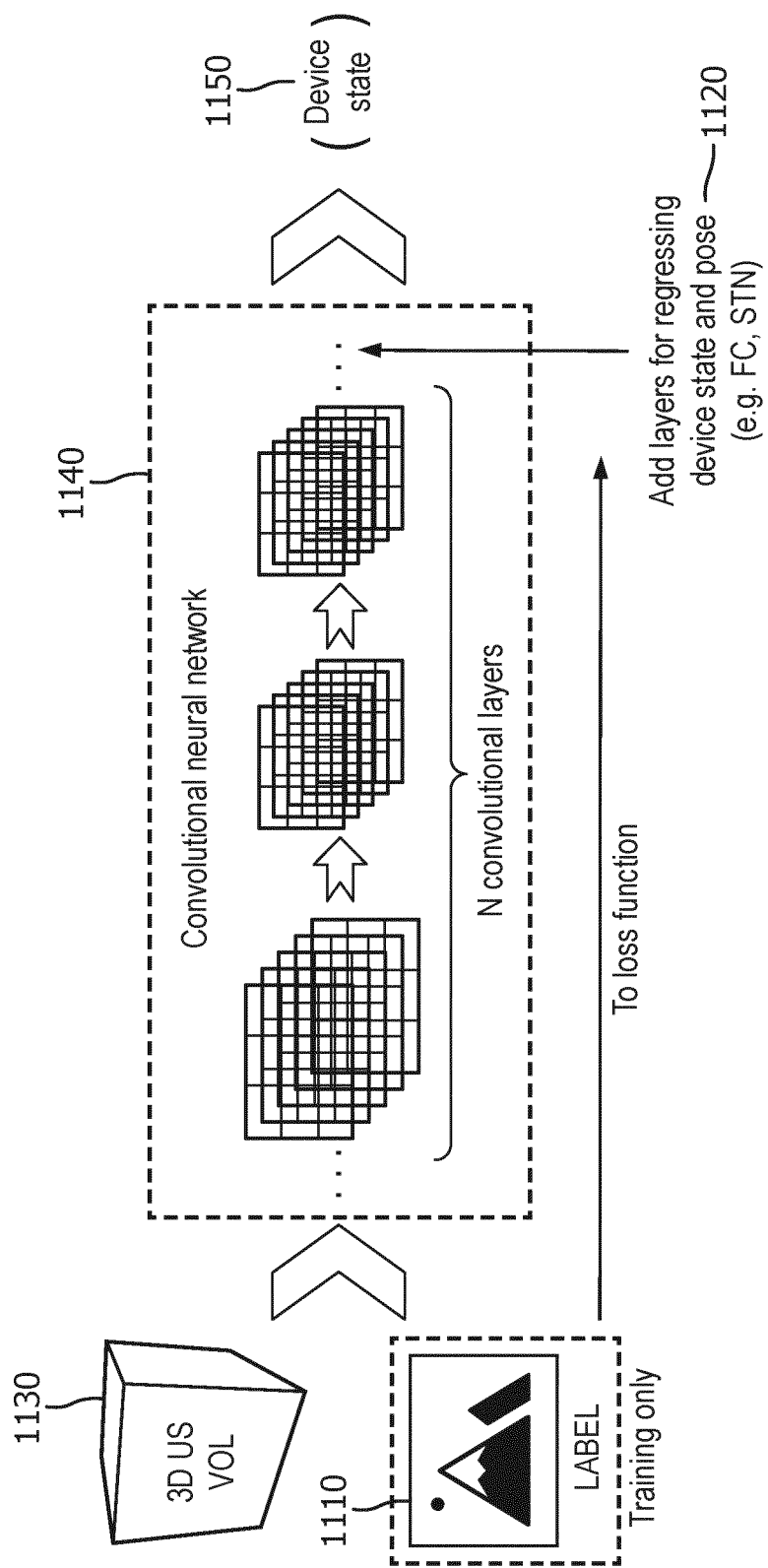
FIG. 11 is a diagrammatic representation of an example convolutional neural network used for determining the state and pose of a transcatheter device end effector, in accordance with at least one embodiment of the present disclosure.

FIG. 11 is a diagrammatic representation of an example convolutional neural network (CNN) 1140 used for determining the state and pose of a transcatheter device end effector, in accordance with at least one embodiment of the present disclosure. In some embodiments, the device state can be derived based on the ability of convolutional neural networks to model complex patterns observed in natural and medical images. This data-driven method can be used to directly derive device state from the 3D image data 1130, and/or by distilling the image features down to a set of precursor parameters as inputs to a conventional image processing method (like the one described above). An example approach is to utilize the supervised learning paradigm where the network 1140 is trained on a large quantity of labeled image data 1110 to produce network layers 1120 for regressing the state and pose of the end effector. The labels can be rigid priors that describe (a.) the state of the end effector, (b.) the pose of the end effector, and (c.) the location of the device within the ultrasound coordinate system of the 3D volume data 1130. This approach can be used to fit a model directly and determine an output vector 1150 that can include for example the pose, state, and position of the end effector. Depending on the computational capacity available, this method may be run in an 'on-demand' manner, as a complement to a more conventional algorithm such as those described hereinabove. The neural network 1140 can take a variety of forms in the architectural sense (e.g. recurrent networks) as well as paradigms (e.g. unsupervised learning, reinforcement learning, etc.) that are known in the art.

In some embodiments, a deep learning (DL) algorithm may begin with a 3D grid to come up with a coarse estimate of where the device may be in the 3D volume 1130. The inclusion of X-ray images as DL inputs may increase robustness. In other embodiments, a 2D ultrasound probe is swept across the volume of interest to generate a 3D image volume 1130.

As described hereinabove, providing redundancy in the user feedback system is beneficial for (a.) repeatably understanding device state—particularly when interacting with tissue, (b.) lowering the barrier for entry and reducing the learning curve for this procedure, and (c.) improving confidence and outcomes of transcatheter MIS procedures.

In some embodiments, the end effector state estimation system 100 is able cross-reference device states based on mechanical manipulation and image-derived states to provide a high degree of redundancy in the case where either input drops below its specific confidence metric. A realistic case scenario can involve poor image appearance of the end effector, and corresponding difficulty of determining the end effector pose and state, in ultrasound images due to shadowing, dropout, or over-gain used to visualize tissue, as well as potential shadowing or foreshortening in X-ray images. In particular, the visualization of grippers is beneficial during the leaflet insertion and grasping step. This is often a challenge, and the end effector state estimation system 100 can provide this missing information based for example on the measured state of control surfaces. The end effector state estimation system 100 can also improve the performance of image-based methods, as it can reduce the optimization search space in the case of poor image features.

The end effector state estimation system 100 can be implemented as a weighted sum of the outputs of the physical and image-based modules using conventional techniques or as a machine-learning (ML) regression problem. Visualization and feedback can be presented to the user via display modules currently in existence, as described for example in U.S. Publication No. 2019/0371012, filed Jan. 15, 2018, and U.S. Provisional Application No. 63/042,801, filed Jun. 23, 2020, both of which are hereby incorporated by reference in their entireties. In some embodiments, the end effector state estimation system 100 may issue recommendations (e.g., text or graphical instructions) to the user about appropriate control surface movements to achieve the desired states for the end effector at different times during the procedure.

Figure 12:
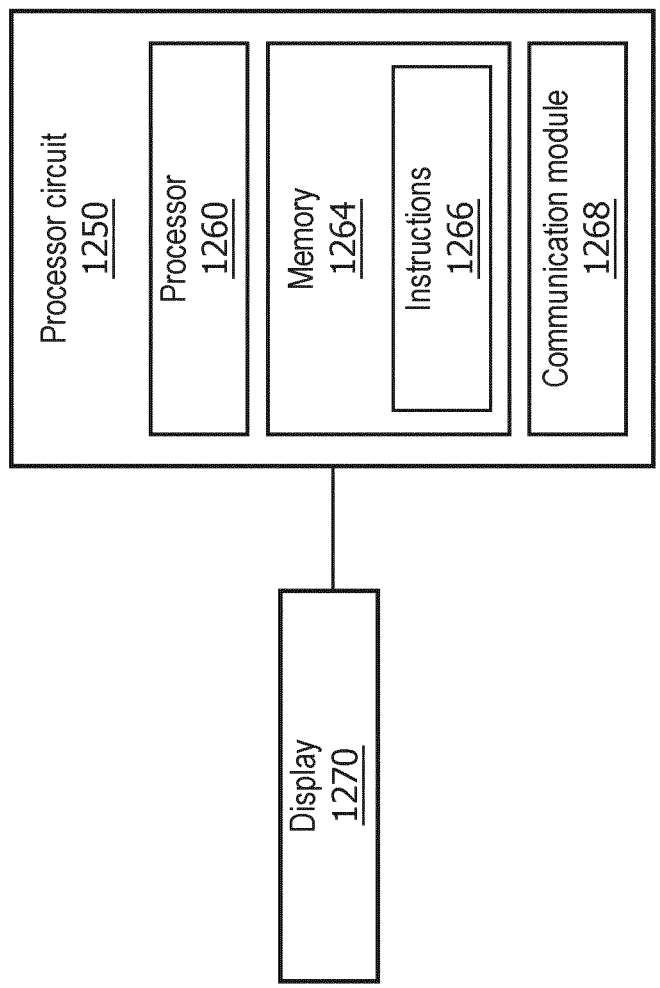
FIG. 12 is a schematic diagram of a processor circuit, according to embodiments of the present disclosure.

FIG. 12 is a schematic diagram of a processor circuit 1250, according to embodiments of the present disclosure. The processor circuit 1250 may be implemented in the ultrasound imaging system 140, or other devices or workstations (e.g., third-party workstations, network routers, etc.), or on a cloud processor or other remote processing unit, as necessary to implement the method. As shown, the processor circuit 1250 may include a processor 1260, a memory 1264, and a communication module 1268. These elements may be in direct or indirect communication with each other, for example via one or more buses.

The processor 1260 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 1260 may also comprise another hardware device, a firmware device, or any combination thereof configured to perform the operations described herein. The processor 1260 may also be implemented as a combination of computing devices, e.g., a combination of a DSP and a microprocessor, a plurality of microprocessors, one or more microprocessors in conjunction with a DSP core, or any other such configuration.

The memory 1264 may include a cache memory (e.g., a cache memory of the processor 1260), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 1264 includes a non-transitory computer-readable medium. The memory 1264 may store instructions 1266. The instructions 1266 may include instructions that, when executed by the processor 1260, cause the processor 1260 to perform the operations described herein. Instructions 1266 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements. Outputs of the processor circuit 1250 may in some instances be visible on a display 1270.

The communication module 1268 can include any electronic circuitry and/or logic circuitry to facilitate direct or indirect communication of data between the processor circuit 1250, and other processors or devices. In that regard, the communication module 1268 can be an input/output (I/O) device. In some instances, the communication module 1268 facilitates direct or indirect communication between various elements of the processor circuit 1250 and/or the ultrasound imaging system 140. The communication module 1268 may communicate within the processor circuit 1250 through numerous methods or protocols. Serial communication protocols may include but are not limited to US SPI, I²C, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or any other appropriate subsystem.

External communication (including but not limited to software updates, firmware updates, preset sharing between the processor and central server, or readings from the ultrasound device) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

As will be readily appreciated by those having ordinary skill in the art after becoming familiar with the teachings herein, the end effector state estimation system can incorporate information from surgical device control surfaces, ultrasound imaging volumes, and 2D X-ray images, and can generate image enhancements or annotations that provide clear, real-time guidance as to the location, pose, and state of a transcatheter surgical device end effector. Accordingly, it can be seen that the end effector state estimation system fills a long-standing need in the art, by reducing the amount of skill and training required to interpret the images used to perform image-intensive, transcatheter, minimally invasive surgical procedures. The output can take for form of guidance overlays and associated visualizations on ultrasound and X-ray images during MIS procedures such as mitral valve leaflet repair. In some embodiments, the system may include physical modifications of the device with electromechanical sensors feeding into a control unit, and/or the presence of spatial tracking systems and corresponding fiducials on the mechanical manipulators. The system can be employed to reliably and repeatably derive the accurate state of implantable devices or end effectors as described above.

A number of variations are possible on the examples and embodiments described above. For example, the system may employ advanced visualization based on onscreen rendering, rendering 3D virtual space via augmented reality (AR) and virtual reality (VR) techniques. The system can be utilized to detect and/or trigger the necessary tissue-specific imaging presets for the ultrasound or X-ray imaging systems based on the end effector state. The system can also be utilized to create new device-specific imaging presents on the ultrasound and X-ray imaging platforms which improve the navigation experience. The end effector state estimation system may perform calculations based on 2D ultrasound images rather than 3D ultrasound volumes, or based on 3D rather than 2D X-ray image data. Other imaging modalities may be used instead of or in addition to those listed above, including but not limited to intracardiac echocardiography (ICE), trans-thoracic ultrasound, intravascular ultrasound (IVUS), etc.

Accordingly, the logical operations making up the embodiments of the technology described herein are referred to variously as operations, steps, objects, elements, components, or modules. Furthermore, it should be understood that these may occur or be arranged or performed in any order, unless explicitly claimed otherwise or a specific order is inherently necessitated by the claim language.

It should further be understood that the described technology may be employed in other types of medical procedures, including veterinary procedures, and may further be employed in non-medical procedures where a transcatheter end effector is employed, and where detailed real-time knowledge of the end effector state is necessary for performance of the procedure.

All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the end effector state estimation system. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." The word "comprising" does not exclude other elements or steps, and the indefinite article "a" or "an" does not exclude a plurality. Unless otherwise noted in the claims, stated values shall be interpreted as illustrative only and shall not be taken to be limiting.

The above specification, examples and data provide a complete description of the structure and use of exemplary embodiments of the end effector state estimation system as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter.

Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. A system for determining a deployment state of a therapeutic device, the system comprising:
   at least one sensor configured to measure at least one parameter related to the deployment state of the therapeutic device,
   wherein the therapeutic device is coupled to a distal portion of a flexible elongate member positioned within a body cavity of a patient and changes shape during deployment, and
   wherein each deployment state corresponds to a different shape of the therapeutic device; and
   a processor configured to:
      receive: (i) image data obtained by an imaging system, wherein the image data is representative of the therapeutic device positioned within the body cavity of the patient, and (ii) the at least one parameter;
      determine the deployment state of the therapeutic device based on the image data and the at least one parameter; and
      output, to a display in communication with the processor, a graphical representation of the deployment state of the therapeutic device.

2. The system of claim 1, wherein the processor is configured to output, to the display, a screen display comprising:
   an image of the body cavity of the patient generated based on the image data; and
   the graphical representation of the deployment state of the therapeutic device overlaid on the image of the body cavity.

3. The system of claim 2, wherein the graphical representation of the deployment state of the therapeutic device comprises a visualization of a three-dimensional model of the therapeutic device.

4. The system of claim 1, wherein the at least one parameter comprises at least one of a position or an angle of a control of the therapeutic device.

5. The system of claim 1, wherein the system comprises a transcatheter delivery device, the transcatheter delivery device comprising the flexible elongate member, and wherein the at least one parameter comprises at least one of a position or an angle of the transcatheter delivery device.

6. The system of claim 5, wherein the at least one sensor comprises an encoder coupled to a mechanical control of the transcatheter delivery device.

7. The system of claim 5, wherein the at least one sensor comprises a magnetic sensor configured to measure the at least one parameter by obtaining position measurements of magnetic seeds positioned on the therapeutic device.

8. The system of claim 1, wherein the imaging system comprises an ultrasound imaging system.

9. The system of claim 1, wherein the imaging system comprises an X-ray imaging system.

10. The system of claim 1, wherein the processor is configured to determine the deployment state of the therapeutic device by using image recognition to match an image generated based on the image data to a model of the therapeutic device.

11. The system of claim 10, wherein the at least one parameter comprises a deployment measurement, and wherein the processor is configured to:
    determine a confidence level of the matched model; and
    determine, when the confidence level is below a threshold value, the deployment state based on the deployment measurement.

12. A method for determining a deployment state of a therapeutic device, the method comprising:
    with a sensor, measuring at least one parameter related to the deployment state of the therapeutic device;
    obtaining, with an imaging system, images including the therapeutic device,
    wherein the therapeutic device is coupled to a distal portion of a flexible elongate member positioned within a body cavity of a patient and changes shape during deployment, and
    wherein each deployment state corresponds to a different shape of the therapeutic device;

with a processor:
- determining the deployment state of the therapeutic device based on the images and the at least one parameter; and
- outputting, to a display in communication with the processor, a graphical representation of the deployment state of the therapeutic device.

13. The method of claim 12, wherein the method comprises outputting, to the display, a screen display comprising:
- at least one of the images; and
- the graphical representation of the deployment state of the therapeutic device overlaid on the at least one image.

14. The method of claim 12, wherein the at least one parameter comprises a position or angle of a control of the flexible elongate member.

15. The method of claim 12, wherein the at least one parameter comprises a position or angle of the therapeutic device.

16. The method of claim 12, wherein the imaging system comprises an ultrasound imaging system.

17. The method of claim 12, wherein the imaging system comprises an X-ray imaging system.

18. The method of claim 12, wherein the sensor comprises a magnetic sensor, and wherein measuring the at least one parameter comprises obtaining position measurements of magnetic seeds positioned on the therapeutic device.

19. The method of claim 12, wherein combining information from the sensor and the imaging system to determine the deployment state of the therapeutic device comprises using image recognition to match an image from the imaging system to a model of the therapeutic device.

20. A system for determining a deployment state of a therapeutic device, the system comprising:
- a mitral valve clip placement device comprising:
  - a catheter; and
  - a mitral valve clip coupled to a distal portion of the catheter;
- an ultrasound imaging device configured to obtain ultrasound images of the mitral valve clip positioned within a body cavity of a patient;
- an X-ray imaging device configured to obtain X-ray images of the mitral valve clip positioned within the body cavity of the patient;
- a sensor coupled to the mitral valve clip placement device and configured to provide a sensor signal indicating a parameter related to the deployment state of the mitral valve clip; and
- a processor configured to:
  - determine, based on the parameter and the X-ray images, a deployment state of the mitral valve clip; and
  - output, to a display in communication with the processor:
    - at least one of the ultrasound images; and
    - a graphical representation of the deployment state of the therapeutic device.

* * * * *